United States Patent [19]

Gammell

[11] 4,346,715
[45] Aug. 31, 1982

[54] HYPERTHERMIA HEATING APPARATUS

[75] Inventor: Paul M. Gammell, Altadena, Calif.

[73] Assignee: The United States of America as represented by the Administrator of the National Aeronautics and Space Administration, Washington, D.C.

[21] Appl. No.: 149,526

[22] Filed: May 13, 1980

Related U.S. Application Data

[63] Continuation of Ser. No. 918,705, Jul. 12, 1978, abandoned.

[51] Int. Cl.$^3$ .............................................. A61N 1/32
[52] U.S. Cl. .................................. 128/422; 128/784; 128/804
[58] Field of Search ........................ 128/1.3–1.5, 128/420 A, 784, 864, 422, 799

[56] References Cited

U.S. PATENT DOCUMENTS

| | | | |
|---|---|---|---|
| 3,096,768 | 7/1963 | Griffith, Jr. | 128/420 A |
| 3,543,761 | 12/1970 | Bradley | 128/784 |
| 3,895,639 | 7/1975 | Rodler | 128/420 A |
| 3,991,770 | 11/1976 | LeVeen | 128/804 |
| 4,016,886 | 4/1977 | Doss et al. | 128/784 |
| 4,095,602 | 6/1978 | LeVeen | 128/804 |
| 4,108,147 | 8/1978 | Kantor | 128/804 |

Primary Examiner—Lee S. Cohen
Attorney, Agent, or Firm—Thomas H. Jones; John R. Manning

[57] ABSTRACT

The present invention is an improved array of electrodes for use in delivering electromagnetic energy to a localized area of a patient's body in a hyperthermic treatment so that it provides a uniform distribution of electromagnetic flux lines within the localized area of the patient's body in order to produce a uniform and localized heating gradient. The improved array of electrodes includes a plurality of electrodes which are arranged in pair, with the electrodes in each pair being spaced a particular distance apart. The improved array of electrodes are driven by a balanced line system which is electromagnetically coupled to each pair of electrodes and which is shielded by a ground coaxial shield which itself is ground to the body of the patient. Each electrode is embedded in a Teflon stand-off in order to move the region of strong field, from the body, produced by rapidly changing potentials. The two pairs of electrodes forming a cross like geometry are used with the balanced line systems. The electrical power is either multiplexed among the electrodes or the second pair is driven by a potential which is sinusoidal and which is 90° out of phase with the first balanced line system which is also sinusoidal.

7 Claims, 5 Drawing Figures

HYPERTHERMIA HEATING APPARATUS

ORIGIN OF THE INVENTION

The invention described herein was made in performance of work under a NASA contract and is subject to the provisions of Section 305 of the National Aeronautics and Space Act of 1958, Public Law 85-568 (72 Stat. 435; 42 USC 2457).

This is a continuation of application, Ser. No. 918,705, filed July 12, 1978, now abandoned.

BACKGROUND OF THE INVENTION

1. Field of the Invention

The present invention relates to hyperthermia, which is the use of heat to selectively destroy cancer cells, and more particularly to a technique for obtaining field homogeneity in hyperthermia.

2. Description of the Prior Art

Hyperthermia has become one of the most rapidly growing areas of cancer research. Methods that are presently in use either involve applications of heat to the entire body of a patient or applications of heat to a selective portion of the body of the patient. When the method of selective applications of heat is used, the heat is generated by conversion of either ultrasonic energy or microwave energy within the tissue itself.

U.S. Pat. No. 4,069,827, entitled Diathermy Apparatus, issued to Francis I. Dominy on Jan. 24, 1978, teaches a combination for use with a diathermy apparatus which includes an oscillator that includes a controlled conduction device having a pair of output electrodes and a device for controlling the controlled conduction device in response to a reference voltage for a particular voltage level.

U.S. Pat. No. 4,016,886, entitled Method for Localizing Heating in Tumor Tissue, issued to James D. Doss and Charles W. McCabe on Apr. 12, 1977, teaches a method of treating tumorous tissue in situ which includes heating substantially only the tumorous tissue by placing at least two electrodes in operative relationship, passing radiofrequency current having a frequency less than 1 MHz substantially directly through the tumorous tissue and forming and placing electrodes to shape the field of the radiofrequency current by inserting into the patient's body a plurality of electrically conductive pins on either side of the tumorous tissue with the distance between opposite pins being inversely proportional to the required radiofrequency field intensity and current. The method also includes electrically interconnecting the pins on one side of the tumorous tissue and electrically interconnecting the pins on the other side of the tumorous tissue. The method further includes applying the radiofrequency current to the interconnected pins on both sides of the tumorous tissue.

There have been problems in obtaining uniform heating when microwave and radiofrequency fields are used. In an article, entitled "Therapeutic Applications of Electromagnetic Power," published in the *Proceedings of the I.E.E.E.*, January, 1974, pages 55 to 75, the authors, Arthur W. Guy, Justus F. Lehmann and Jerry B. Stonebridge, discuss diathermy ". . . which is a technique used for producing therapeutic heating in tissue by conversion of physical forms of energy such as ultrasound, EM shortwaves, or microwaves into heat after being transmitted transcutaneously to deep afflicted tissue areas. The technique has been used in physical medicine from the time that the physical energy sources have been available to man." The article traces the history of the use of electromagnetic waves through today's present use of the microwave frequencies of 2450 megahertz and of 915 megahertz in therapeutic uses. The three inch (3") wavelength of the 2450 megahertz microwaves allows directionality thereof, but it is not short enough to allow it to be focused within the body. In order to focus microwave energy to the dimensions in the range of centimeters, the frequency of the microwaves must be in the range of 50,000 to 75,000 megahertz. Although little work has been done in this range of frequencies, it would appear that the attenuation of these microwaves would result in poor penetration into the tissue. There have been reports which indicate that the microwave of a 2450 megahertz frequency can give rise to hot spots in an area a short distance away from a fat-muscle interface which are due to a standing wave effects. These standing waves are not seen if the microwaves of a 915 megahertz frequency are used.

In their paper, entitled "Prediction of Dynamic Temperature Distribution in Normal and Neoplastic Tissues During Diathermy," presented at the 30th Annual Conference for Engineering in Medicine and Biology (30th ACEMB), held in Los Angeles, Calif. on Nov. 5 through 9, 1977, H. P. Stein and R. K. Jain stated:

"Hyperthermia is destructive to cancer cells above 40° C. and is lethal to normal cells of the host tissue at a temperature above 42° C. It is equally harmful in the temperature range of 37.5° C. to 40° C. where metabolism of the tumor cells is progressively increased. Due to this narrow range of operation, a definite need exists to quantify and predict the temperature distribution in the neoplastic and surrounding normal tissues of the host to exploit hyperthermia for the optimal management of cancer."

In their paper, entitled "Clinical Applications of Hyperthermia Techniques in Cancer," also presented at the 30th ACEMB, C. J. Sternhagen, J. M. Larkin, J. D. Doss, P. W. Day, S. Edwards and D. E. Smith stated:

"Localized current field techniques using 500 kilohertz radiofrequency current have been used in oral cavity and other accessible malignancies. This frequency has the advantage of allowing the physician to continuously monitor the temperature by the use of surface thermistors as well as thermistors placed directly into the tumor or adjacent normal tissue. Continuous monitoring of the treatment temperature has been one of the criteria of clinical protocols used, and appears to be essential to developing the hyperthermia techniques while maintaining patient safety—because great variations of temperatures occur at times at ranges within a few millimeters. The first localized hyperthermia technique used in human patients in this series was basically a non-invasive technique involving the use of electrode plates placed so that the most hypoxic portion of the malignancies would receive the highest temperature in the treatment volume, while normal structures would be relatively spared by receiving a lower temperature. This has the advantage of delivering the heat where the tumor is most likely to be resistant to radiation treatment: the hypoxic center of the tumor. It has the disadvantage of being somewhat less capable of delivering a homogenous hyperthermia treatment to deeper tumor structures. Another localized hyperthermia technique used consisted in the placement of needles in an invasive biplanar interstitial implant configuration. The needles are placed surrounding the tumor in two parallel rows with the control thermistor and monitor thermistors arrayed appropriately between the rows of needles. Using these localized methods a treatment can be maintained for periods up to thirty minutes during which the temperature will fluctuate less than one degree centigrade [(1° C.)]. This is usual treatment time currently in use. The temperature currently in use is in the range of 42 to 44 degrees C., with shorter durations of heating employed if the temperature approaches the higher range."

Hyperthermia is often used in synergism with ionizing radiation to produce cell destruction which is selective toward cancer cells. When hyperthermia of the whole body mode is used, the only selectivity is the differential response of cancer cells to an elevated temperature. However, when hyperthermia of the local heating mode is used, the object is to produce a temperature rise of one degree to four degrees Centigrade (1° to 4° C.) at the site of the cancer cells. Local hyperthermia is usually produced by absorption of either ultrasonic energy or electromagnetic energy and its conversion to heat within the tissue. When either source of energy is used, consideration must be given to the design of the applicator and the interaction between the electromagnetic or ultrasonic field and the tissue so that uniform heating is obtained in the desired region of application with minimal insult to other tissues.

Some of the solutions to the problems which are associated with induced hyperthermia through interstitially implanted electrodes have been attempted with varying degrees of success. Several of these techniques are: (1) reducing current density by using lower power; (2) increasing the contact area by the use of more needles; (3) actively cooling the electrodes; and (4) using some other configuration of electrodes.

The University of Arizona Medical Center is perhaps the medical center with the greatest experience in the utilization of interstitially implanted electrodes for the induction of localized hyperthermia. Although the results have been admirable and overall encouraging, some unexpected morbidity has been experienced in some of the treated animals which is attributable to localized "hot spots." At present there are satisfactory methods of avoiding "hot spots" including those listed above. The first technique could result in reduced effectiveness of induced hyperthermia, and, if the tumor temperature does not at least reach 41.5° C., result even in a possible enhancement of tumor growth. The utilization of the second technique could result in a less than optimum tumor radiation dose if the needles are implanted too close together in order to increase the contact area for hyperthermia treatment (unless nonradioactive needles are interdispersed with radioactive ones). The third technique is impractical for an interstitial implant except for that region of the implanted needle protruding from the skin. The fourth technique has not been developed until the present invention.

SUMMARY OF THE INVENTION

In view of the foregoing conditions and factors characteristic of the prior art it is a primary object of the present invention to provide a hyperthermic technique which produces a uniform heating gradient within a localized area of a patient's body.

It is another object of the present invention to provide a hyperthermic technique which eliminates "hot spots" at a fat-muscle interface which are due to standing waves.

It is still another object of the present invention to provide a hyperthermic technique which eliminates "hot spots" which are due to a concentration of electromagnetic flux lines that are formed at a single pair of electrodes.

It is yet another object of the present invention to provide a hyperthermic technique in which several pairs of electrodes are electromagnetically coupled together and in which the excitation source is commutated among the pairs of electrodes in order to minimize local field gradients and to reduce any local heat build-up in the locality of the electrodes.

It is yet still another object of the present invention to provide a hyperthermic technique in which a Teflon shield is placed between the coaxial shield of each electrode and the skin so that most of the diverging field will occur within the Teflon shield rather than in the skin or fat in order to prevent the fat from heating up.

In accordance with an embodiment of the present invention an improved array of electrodes for use in delivering electromagnetic energy to a localized area of a patient's body in hyperthermic treatment so that it provides a uniform distribution of electromagnetic flux lines within the localized area of the patient's body in order to produce a uniform and localized heating gradient is described. The improved array of electrodes includes a plurality of electrodes which are arranged in pairs, with the electrodes in each pair being spaced a particular distance apart. In one embodiment there are two pairs of electrodes being spaced twice the particular distance of the electrodes of each pair. In another embodiment there are additionally two pairs of electrodes which are disposed orthogonally to the first two pairs of electrodes and which are similarly spaced apart from each other. The improved array of electrodes are driven by a balanced line system which is electromagnetically coupled to each pair of electrodes and which is shielded by a coaxial shield which itself is grounded to the body of the patient. Each electrode is embedded in a Teflon stand-off in order to move the region of strong field produced by rapidly changing potentials away from the skin and fat of the patient. The balanced line system is multiplexed between the first two pairs of electrodes and the second two pairs of electrodes in the second embodiment. A second balanced line system which is sinusoidal and which is 90° out of phase with the first balanced line system which is also sinusoidal may be used instead of multiplexing.

The features of the present invention which are believed to be novel are set forth with particularity in the appended claims.

Other objects and many of the attendant advantages will be more readily appreciated as the same becomes better understood by reference to the following detailed description and considered in connection with the accompanying drawing in which like reference symbols designate like parts throughout the figures.

DESCRIPTION OF THE PREFERRED EMBODIMENT

Figure 1:
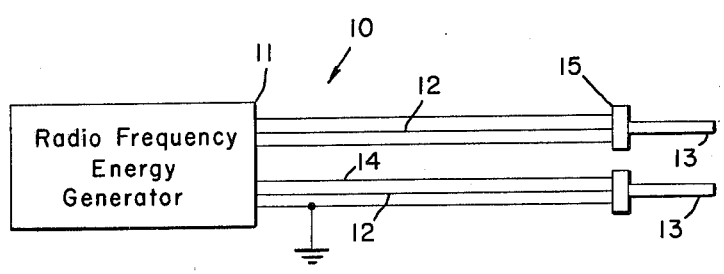
FIG. 1 is a schematic drawing of an apparatus for delivering electromagnetic energy to a localized area of a patient's body in a hyperthermic treatment.

In order to best understand the present invention it is necessary to first read the foregoing description of an apparatus for delivering electromagnetic energy to a localized area of a patient's body in a hyperthermic treatment in conjunction with reference to the accompanying drawing. Referring to FIG. 1 a hyperthermic apparatus 10 includes a radiofrequency energy generator 11 a plurality of positive and negative conductors 12 which are electromagnetically coupled to the radiofrequency energy generator 11 and a plurality of electrodes 13 which are interstitially implanted into the body of a patient. In the preferred embodiment the conductors 12 are each shielded by a grounded coaxial shield 14 which is grounded and which is electrically coupled to the body of the patient. A balanced line system is provided in which the electrodes 13 are driven with equal and opposite voltages with the body of the patient being grounded to a system that is at the equipotential point. The use of the balanced line system provides excellent control over the stray fields and current paths. Since the frequency that is most commonly used in current hyperthermia research is 500 kilohertz a balanced line technique is practical with inexpensive transformers being available to convert a single ended power amplifier to a balanced line.

Figure 2:
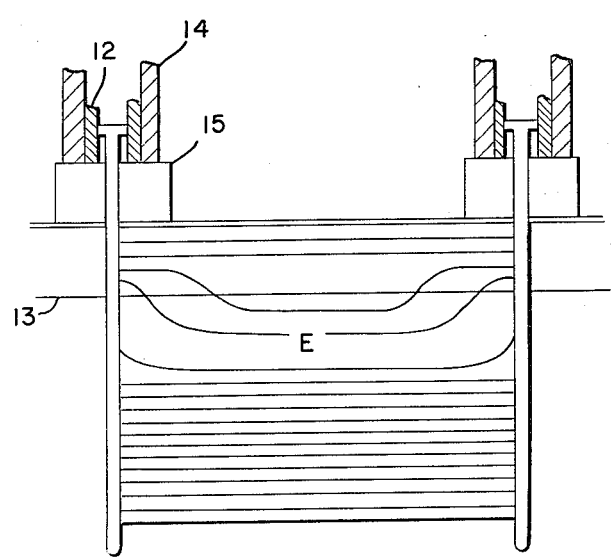
FIG. 2 is a cross-sectional view of a pair of electrodes, which are needles adapted to receive radio frequency energy, each of which electrodes is shielded by a grounded coaxial shield and insulatively coupled to a Teflon stand-off at the air/skin interface in accordance with the principles of the present invention.

Referring now to FIG. 2 in conjunction with FIG. 1 the electrodes 13 and the coaxial shield 14 are mechanically coupled to Teflon stand-offs 15 at the air/skin interfaces. The Teflon stand-offs serve both as devices for moving the regions of strong fields, which are due to rapidly changing potentials, away from the localized area of the body of the patient and as insulating devices which insulate the fat and skin adjacent thereto from the heat generated. Dielectric materials other than the Teflon are suitable.

In tissue dielectric dispersion and subsequent absorption are expected to contribute significantly only at microwave frequencies. At lower frequencies, in the range of kilohertz to low megahertz, the absorption in tissue is due entirely to ionic conduction. Therefore the technology for controlling the area of application of radiofrequency energy waves will be different than the technology for microwave energy waves. The wavelength of the radiofrequency energy waves is so long compared with any dimensions of the body of the patient that spatial propagation effects, such as standing waves, focusing and propagation direction can be ignored. The region of therapy can be controlled by selecting the geometry of the electrodes and their placement with due regard to temporal phase shifts. This becomes especially attractive when the electrodes are needles which are already in place as interstitial implants of radioactive materials as in endoradiotherapy and which can then function as an array of electrodes 13.

At radiofrequencies in the range of 100 kilohertz to 50 megahertz the wavelength is much longer than the dimensions of the area being treated. The calculations of the field and the anticipated heating patterns may be based on a quasi-static analysis in which propagation effects are neglected. The difference in the field intensity at different locations is determined by the electrode geometry and by the dielectric constants of the tissue and of any insulators present.

Figure 3:
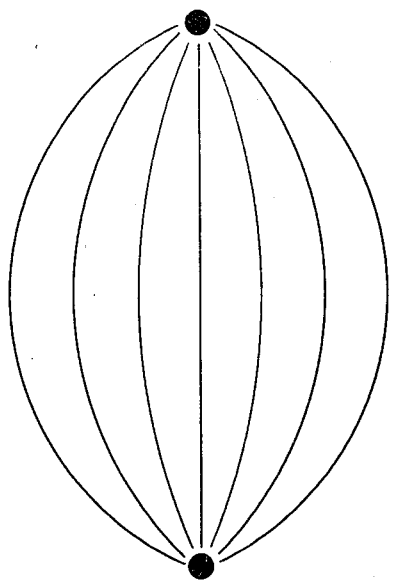
FIG. 3 is a diagram of lines of force of a prior art array of electrodes.

As the inventor has previously mentioned in the Description of the Prior Art, Radium-226 needles have been employed as radiofrequency current electrodes 13 in animal implant therapy. In this therapy there have been localized "hot spots" observed in the region of the needles. This particular problem has been most acute when only two needles are used as electrodes 13 in which case the field gradient would be the greatest adjacent to the needles. Referring to FIG. 3 one can observe the field of force of prior art array of two electrodes 13.

Referring again to FIG. 2 the Teflon stand-offs 15 and the coaxial shields 14 are shown mechanically coupled to the pair of electrodes 13. The grounded coaxial shields 14 eliminate or reduce the stray fields by shielding the conductors 12 to the electrodes 13. However, if the shields 14 are brought too close to the skin the strongly diverging fields between the electrodes 13 and the shields 14 will produce high intensity fields in the skin or subcutaneous fat thereby resulting in "hot spots." The purpose of the Teflon stand-offs 15 is to move the region of strong fields away from the body of the patient. Little interruption of the field takes place at the skin/Teflon interface because both have approximately the same dielectric constants. Furthermore, since the dielectric constant of muscle is 50 as compared to the dielectric constant of 5 for fat, most of the field will be drawn into the muscle or tumor. Additionally, since fat has a lower conductivity, a lesser portion of the field that does result in the fat will be converted into heat and the larger portion of the thermal energy will be deposited in the muscle or tumor. The use of the balanced line system in conjunction with the coaxial shields 14 and the Teflon stand-offs 15 meets the requirement of depositing most of the energy in the muscle layer.

Figure 4:
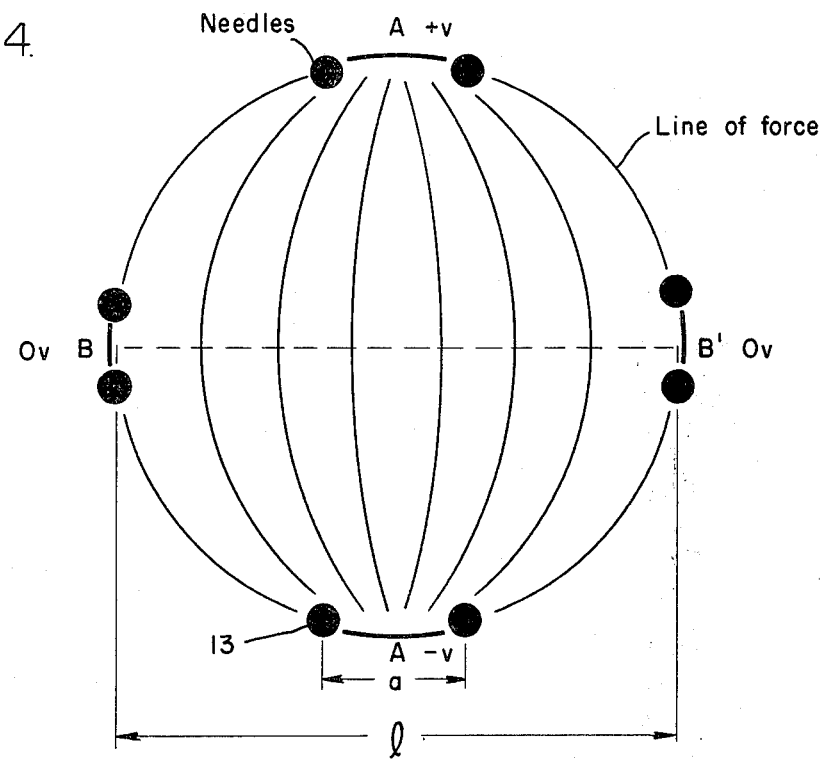
FIG. 4 is a diagram of lines of force of an improved array of electrodes which are arranged in accordance with the principles of the present invention.

The requirement that the field be uniform is met by an improved array of electrodes 13 which includes a plurality of sets with each set having two electrodes, each electrode 13 in each set of two electrodes is spaced a particular distance apart from the other electrode 13. Referring briefly again to FIG. 3 it can be seen that a pair of point electrodes 13 gives a field that converges sharply around the point electrodes 13 thereby resulting in large field gradients. The sketch is intended as an approximation of the field lines which can be rigorously calculated from the Laplace equations. The solution to the Laplacian which avoids the strong fields in the vicinity of the electrodes 13 is to replace the single pair of electrodes 13 with an array of electrodes 13 as shown in FIG. 4. The field concentration in the vicinity of the set of electrodes 13 is reduced by the connecting the two sets of electrodes together in order to avoid the rapidly converging field near each set of electrodes 13. This results in a field near each set of electrodes 13 that is not nearly as strong as compared to the central field as it is with the single pair of electrodes 13. The heating near each set of electrodes 13 could be made to approximately twice that in the central region by choosing the spacing of the electrodes appropriately.

In FIG. 4 there is a first two sets of electrodes 13 which are spaced apart from each other a distance, 1, which is twice the particular distance, a, that each set of electrodes 13 are spaced apart (1=2a). There is also a second two sets of electrodes which are disposed orthogonally to the first two sets of electrodes and similarly spaced apart from each other.

Figure 5:
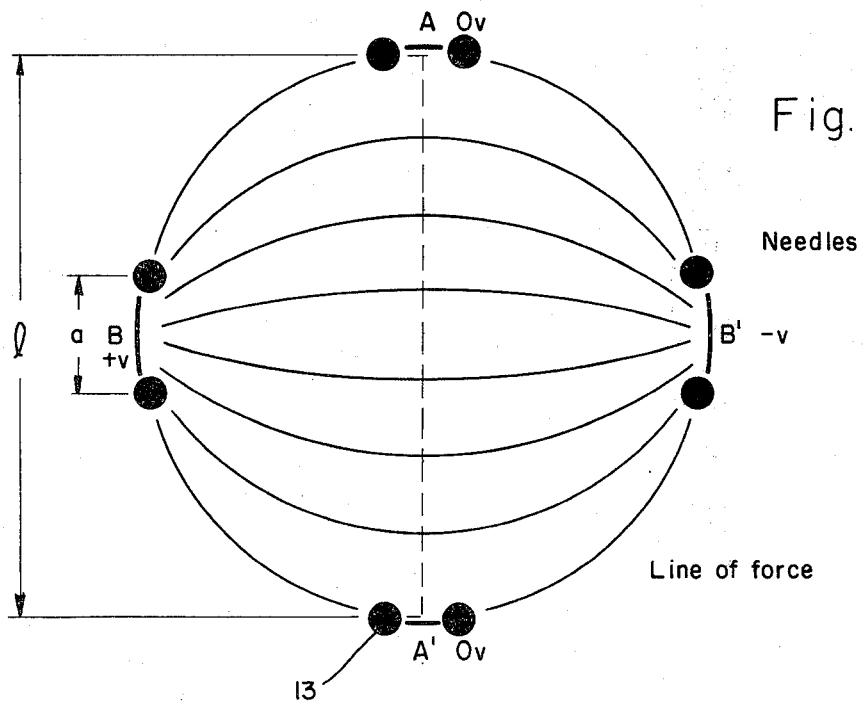
FIG. 5 is a diagram of lines of force of the improved array of electrodes of FIG. 4 after the balanced line system has been multiplexed to the second two pairs of electrodes. The field lines would be the same after a 90° phase shift if phase shifting instead of multiplexing were used.

Still referring to FIG. 4 the balance line system provides a sinusoidal power signal to the improved array of electrodes 13. In order to achieve additional uniformity of the field the balanced line system could be multiplexed to provide a power signal to the first two sets of electrodes 13 and then to the second two sets of electrodes 13 at a rate which is fast in comparison with the heat diffusion rate. Alternatively, the first balanced line system may be coupled to the first two sets of electrodes 13 and a second balanced line system may be coupled to the second two sets of electrodes 13, with the second balanced line system being 90° out of phase with the first balanced line system. The result of this phasing is shown in FIG. 5, after a 90° phase shift of the power signal.

When phasing is used to shift the field between the sets of electrodes, the field is gradually passed from one configuration to another. At the moment of time 45 electrical degrees later than shown in FIG. 4 both of the electrode pairs are excited at seventy percent (70%) of their maximum amplitudes with the resulting field lying at an angle of forty-five geometric degrees (45°) between the sets of electrodes 13. The inventor believes that greater uniformity of heating will be obtained by phasing two balanced line systems rather than by multiplexing a single balanced line system between two sets of electrodes 13.

From the foregoing it can be seen that an improved array of electrodes has been described in conjunction with several devices including a grounded coaxial shield and a Teflon stand-off for use in a hyperthermic technique to provide localized heating in the body of a patient. The primary advantage of the improved array of electrodes is that its structure and its mode of excitation combine the functions of: (1) endocurietherapy which uses radioactive seeding needles and x-rays and gamma-rays; and (2) localized hyperthermia which is induced by exciting structured sets of the needles, functioning as electrodes, with radiofrequency energy in the range of 500 kilogertz by either multiplexing or exciting them in quadrature to cause an isothermal rotating electric field which is confined to the area of the tumor or lesion.

Accordingly it is intended that the foregoing disclosure and showing made in the drawing shall be considered only as illustrations of the present invention. Furthermore it should be noted that the sketches are not drawn to scale and that distances of and between the figures are not to be considered significant. The invention will be set forth with particularity in the appended claims.

What is claimed is:

1. An improved array of electrodes for use in delivering electromagnetic energy to a localized area of a patient's body in a hyperthermic treatment so that said improved array of electrodes provides a uniform distribution of electromagnetic flux lines within the localized area of the patient's body in order to produce a uniform and localized heating gradient, said improved array of electrodes comprising:
   a. a plurality of electrodes which are arranged in sets of electrodes, each of said sets of electrodes having two of said electrodes which are spaced a particular distance apart from each other, pairs of said sets of electrodes being spaced apart a distance which is relatively greater than said particular distance and arranged in oppositely disposed pairs whereby the localized area of the patient's body is disposed between each of said sets of electrodes of each of said pairs of said sets of electrodes; and
   b. electromagnetic energy means for applying electromagnetic energy to each of said pairs of said sets of electrodes.

2. An improved array of electrodes according to claim 1 wherein said plurality of sets of electrodes comprises two of said sets of electrodes in order to avoid a rapidly diverging field near each of said electrodes, each of said sets of electrodes are spaced apart approximately twice the particular distance which said electrodes of each of said sets of electrodes are spaced apart.

3. An improved array of electrodes according to claim 2 wherein said plurality of electrodes comprises an additional two of said sets of electrodes which are disposed orthogonally to said first two of said sets of electrodes and which are similarly spaced apart.

4. An improved array of electrodes according to claim 3 wherein said electromagnetic energy means comprises:
   a. a first balanced line system electromagnetically coupled to the first two of sets of electrodes, said balanced line system providing a sinusoidal energy source; and
   b. a second balanced line system electromagnetically coupled to the second two of sets of electrodes, said balanced line system providing a sinusoidal energy source that is 90° out of phase with the sinusoidal energy source of said first balanced line system.

5. An improved array of electrodes according to claim 3 wherein said electromagnetic energy means comprises:
   a. a multiplexing balanced line system electromagnetically coupled to said plurality of electrodes so that said multiplexing balanced line system can multiplex an energy source to the first two of sets of electrodes and the second two of sets of electrodes alternately in order to achieve a rotating field, the multiplexing is to be done at a rate which is fast in comparison with the time required for diffusion.

6. An improved array of electrodes according to claim 1 wherein said electromagnetic energy means comprises:
   a. a grounded coaxial shield; and
   b. a balanced line system electrically coupled to said array of electrodes for driving said array of electrodes, said balanced line system being shielded by said grounded coaxial shield.

7. An improved array of electrodes according to claim 6 wherein said coaxial shield is disposed in a Teflon stand-off which is adapted to be inserted into the localized area of the patient's body so that is provides means for moving the region of strong fields, which are produced by rapidly, spatially changing potentials, away from the patient's body.

* * * * *